US00PP19089P2

(12) United States Plant Patent
Sakazaki

(10) Patent No.: US PP19,089 P2
(45) Date of Patent: Aug. 12, 2008

(54) *PHLOX* PLANT NAMED 'USPHLO1M'

(50) Latin Name: *Phlox hybrida*
Varietal Denomination: USPHLO1M

(75) Inventor: Ushio Sakazaki, Shiga (JP)

(73) Assignee: Plant 21 LLC, San Marco, CA (US)

( * ) Notice: Subject to any disclaimer, the term of this patent is extended or adjusted under 35 U.S.C. 154(b) by 0 days.

(21) Appl. No.: 11/725,223

(22) Filed: Mar. 16, 2007

(51) Int. Cl.
*A01H 5/00* (2006.01)

(52) U.S. Cl. ..... Plt./320

(58) Field of Classification Search ..... Plt./320
See application file for complete search history.

*Primary Examiner*—Kent L Bell
*Assistant Examiner*—S. B. McCormick Ewoldt
(74) *Attorney, Agent, or Firm*—C. A. Whealy

(57) ABSTRACT

A new and distinct cultivar of *Phlox* plant named 'USPHLO1M', characterized by its upright, outwardly spreading and mounding plant form; vigorous growth habit; freely branching habit and short internodes; dense and busy plant habit; freely and continuous flowering habit; light purple-colored flowers with white-colored centers; and relative tolerance to high temperatures.

1 Drawing Sheet

Botanical designation: *Phlox hybrida.*
Cultivar denomination: 'USPHLO1M'.

BACKGROUND OF THE INVENTION

The present invention relates to a new and distinct cultivar of Phlox, botanically known as *Phlox hybrida* and hereinafter referred to by the name 'USPHLO1M'.

The new *Phlox* is a naturally-occurring branch mutation of the *Phlox hybrida* cultivar USPHL01, disclosed in U.S. Plant Pat. No. 15,608. The new *Phlox* was discovered and selected by the Inventor in a controlled environment in Aichi, Japan on Apr. 20, 2004.

Asexual reproduction of the new *Phlox* by cuttings in a controlled environment in Aichi, Japan since Jun. 8, 2004, has shown that the unique features of this new *Phlox* are stable and reproduced true to type in successive generations.

SUMMARY OF THE INVENTION

The cultivar USPHLO1M has not been observed under all possible environmental conditions. The phenotype may vary somewhat with variations in environmental and cultural practices such as temperature and light intensity without, however, any variance in genotype.

The following traits have been repeatedly observed and are determined to be the unique characteristics of 'USPHLO1M'. These characteristics in combination distinguish 'USPHLO1M' as a new and distinct cultivar of *Phlox:*

1. Upright, outwardly spreading and mounding plant form.
2. Vigorous growth habit.
3. Freely branching habit and short internodes; dense and busy plant habit.
4. Freely and continuous flowering habit.
5. Light purple-colored flowers with white-colored centers.
6. Relatively tolerant to high temperatures.

Plants of the new *Phlox* and the parent, the cultivar USPHL01, differ primarily in flower coloration as plants of the cultivar USPHL01 have purple violet-colored flowers with white-colored centers.

Plants of the new *Phlox* can also be compared to plants of the cultivar Junior Bouquet, disclosed in U.S. Plant Pat. No. 16,865. Plants of the new *Phlox* and the cultivar Junior Bouquet differ primarily in plant form and flower color as plants of the cultivar Junior Bouquet are mostly upright and have dark pink-colored flowers with red purple-colored centers.

BRIEF DESCRIPTION OF THE PHOTOGRAPHS

The accompanying colored photographs illustrate the overall appearance of the new *Phlox,* showing the colors as true as it is reasonably possible to obtain in colored reproductions of this type. Colors in the photographs may differ slightly from the color values cited in the detailed botanical description which accurately describe the colors of the new *Phlox.*

The photograph at the bottom of the sheet comprises a side perspective view of a typical flowering plant of 'USPHLO1M' grown in a container.

The photograph at the top of the sheet is a close-up view of typical flowers and leaves of 'USPHLO1M'.

DETAILED BOTANICAL DESCRIPTION

The aforementioned photographs and following observations, measurements a values describe plants grown in Bonsall, Calif., under commercial practice during the late summer in an outdoor nursery with day temperatures ranging from 18° C. to 38° C. and night temperatures ranging from 16° C. to 24° C. After planting rooted young plants, plants had been growing for about five weeks when the photographs and description were taken. In the following description, color references are made to The Royal Horticultural Society Colour Chart, 1995 Edition, except where general terms of ordinary dictionary significance are used.

Botanical classification: *Phlox hybrida* cultivar USPHLO1M.

Parentage: Branch mutation of the *Phlox hybrida* cultivar USPHL01, disclosed in U.S. Plant Pat. No. 15,608.

Propagation:

*Type.*—By cuttings.

*Time to initiate roots.*—About one to two weeks.

*Time to produce a rooted plant.*—About three to four weeks.

*Root description.*—Fine, fibrous; white in color.

Plant description:

*Plant form/habit.*—Upright, outwardly spreading and mounding plant form; vigorous growth habit. Freely branching habit, about six main laterals each with about five or six secondary laterals; relatively short internodes; dense and bushy plant habit.

*Plant height.*—About 26 cm.

*Plant width* (*spread*).—About 65 cm.

*Lateral branches.*—Length: About 28 cm. Diameter: About 2 mm. Internode length: About 1.5 cm. Strength: Strong. Texture: Pubescent. Color: 144A.

Foliage description:

*Arrangement.*—Alternate, simple; sessile.

*Length.*—About 4.5 cm.

*Width.*—About 9 mm.

*Shape.*—Lanceolate.

*Apex.*—Acuminate.

*Base.*—Clasping to slightly auriculate.

*Margin.*—Entire.

*Texture, upper and lower surfaces.*—Pubescent; slightly glandular; rough.

*Venation pattern.*—Pinnate.

*Color.*—Developing leaves, upper and lower surfaces: 146A. Fully expanded leaves, upper surface: 147B; venation, 147C. Fully expanded leaves, lower surface: 147B; venation, 147B.

Flower description:

*Flower type/habit.*—Single rotate and salverform flowers arranged in short cymes of four to five flowers each; flowers face upright and outward. Freely flowering habit with about 175 flower buds and flowers developing per plant.

*Fragrance.*—None detected.

*Natural flowering season.*—Continuously flowering year round in Southern California. Flowers not persistent.

*Postproduction longevity.*—Flowers last about four to five days on the plant.

*Flower buds.*—Height: About 1.4 cm. Diameter: About 5 mm. Shape: Elliptic. Color: 75D.

*Inflorescence height.*—About 2.7 cm.

*Inflorescence diameter.*—About 4.5 cm to 5.5 cm.

*Flower diameter.*—About 2.7 cm.

*Flower depth.*—About 1.8 cm.

*Flower throat diameter.*—About 1 mm.

*Flower tube length.*—About 1.6 cm.

*Flower tube diameter, at base.*—About 2 mm.

*Petals.*—Quantity per flower: Typically five in a single whorl; petals fused at the base into a narrow tube. Lobe length: About 1.3 cm. Lobe width: About 1.3 cm. Shape: Obovate. Apex: Rounded. Margin: Entire. Texture, petal lobes upper and lower surfaces: Smooth, glabrous; satiny. Texture, throat: Smooth, glabrous. Texture, tube: Pubescent. Color: Developing petals, upper surface: 85C to 85D. Developing petals, lower surface: 69D. Fully expanded petals, upper surface: 77C; towards the base, 78B; at the center, 155A; venation, 78B. Fully expanded petals, lower surface: 76B; venation, 76C. Flower throat: 77C. Flower tube: 76C.

*Sepals.*—Quantity per flower: Typically five in a single whorl, fused towards the base into a slender tube. Length: About 7 mm. Width: About 1 mm. Shape: Lanceolate. Apex: Acuminate. Margin: Entire. Texture, upper and lower surfaces: Pubescent. Color, upper and lower surfaces: 146A.

*Peduncles.*—Length: About 1.6 cm. Diameter: About 1 mm. Angle: Erect to about 45° from vertical. Strength: Strong. Texture: Pubescent. Color: 146C.

*Pedicels.*—Length: About 8 mm. Diameter: About 1 mm. Angle: About 45° to about 55° from peduncle axis. Strength: Strong. Texture: Pubescent. Color: 146C.

*Reproductive organs.*—Stamens: Quantity per flower: Typically five. Anther shape: Oblong. Anther length: About 2 mm. Anther diameter: About 1 mm. Anther color: 13A. Pollen amount: Scarce. Pollen color: 13A. Pistils: Quantity per flower: One. Pistil length: About 5 mm. Stigma shape: Three-parted. Stigma color: 1B. Style length: About 2 mm. Style color: 145C. Ovary color: 150B.

*Seed/fruit.*—Seed and fruit development have not been observed.

Disease/pest resistance: Plants of the new *Phlox* have not been noted to be resistant to pathogens and pests common to *Phlox*.

Garden performance: Plants of the new *Phlox* have been observed to have good garden performance and tolerate rain, wind and temperatures ranging from about 0° C. to about 40° C.; relatively tolerant to high temperatures.

It is claimed:

1. A new and distinct *Phlox* plant named 'USPHLO1M' as illustrated and described.

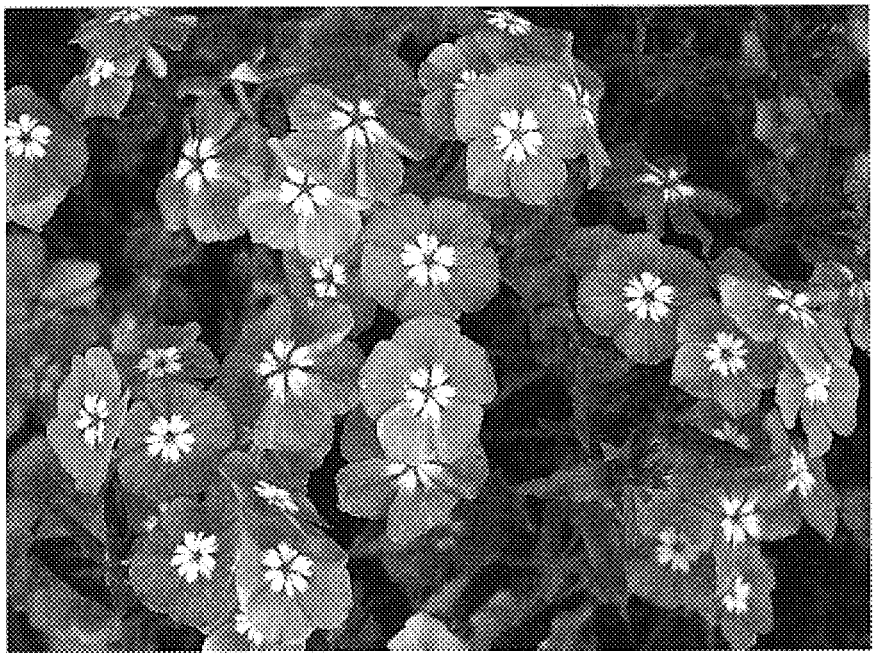
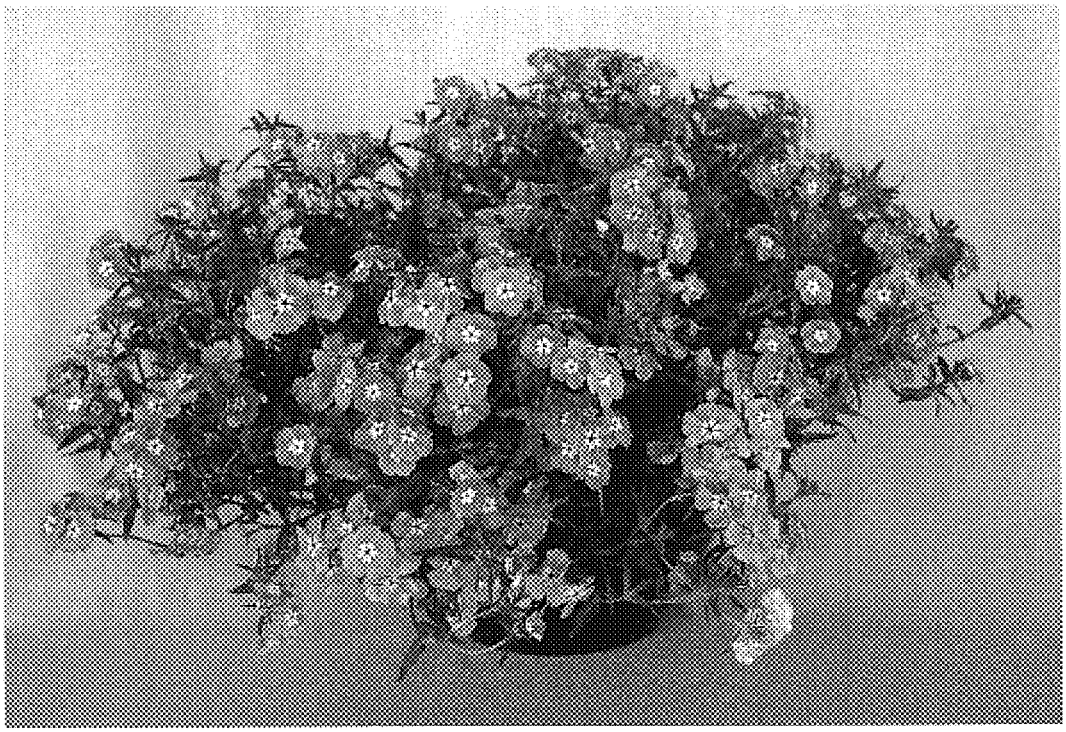

* * * * *